(12) United States Patent
Mitra et al.

(10) Patent No.: US 7,838,479 B2
(45) Date of Patent: *Nov. 23, 2010

(54) PACKAGED PRODUCT CONTAINING AN EXTRUDABLE MULTIPHASE COMPOSITION OF A FREE FATTY ACID PHASE AND A SOAP PHASE

(75) Inventors: Shuman Mitra, Dublin, CA (US); Sudhakar Puvvada, Shelton, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 978 days.

This patent is subject to a terminal disclaimer.

(21) Appl. No.: 10/457,179

(22) Filed: Jun. 9, 2003

(65) Prior Publication Data

US 2004/0248749 A1    Dec. 9, 2004

(51) Int. Cl.
*A61K 7/50* (2006.01)

(52) U.S. Cl. .................. 510/130; 510/156; 510/488; 510/492

(58) Field of Classification Search ........... 510/406, 510/120, 121, 122, 130, 158, 159, 404; 424/401; 514/844

See application file for complete search history.

(56) References Cited

U.S. PATENT DOCUMENTS

| 3,694,367 | A |   | 9/1972 | Peters et al. |
| 5,612,307 | A | * | 3/1997 | Chambers et al. ........... 510/406 |
| 5,891,834 | A |   | 4/1999 | Chopra et al. |
| 5,929,019 | A | * | 7/1999 | Puvvada et al. ............. 510/406 |
| 6,080,708 | A | * | 6/2000 | Glenn et al. ................. 510/130 |
| 6,534,456 | B2 |  | 3/2003 | Hayward et al. |
| 6,534,457 | B2 |  | 3/2003 | Mitra |
| 6,689,223 | B1 | * | 2/2004 | Meine et al. ................... 134/2 |

FOREIGN PATENT DOCUMENTS

| WO | 95/02035 | 1/1995 |
| WO | 97/11148 | 3/1997 |
| WO | 01/80821 | 11/2001 |

OTHER PUBLICATIONS

European Search Report, EP 04 25 3292, dated Sep. 21, 2004—2 pp.

* cited by examiner

*Primary Examiner*—Necholus Ogden, Jr.
(74) *Attorney, Agent, or Firm*—Alan A. Bornstein

(57) ABSTRACT

The invention relates to a cleansing composition product having at least one acid phase and at least one soap phase that are separated. The inventive composition is contained in a partitioned container in one embodiment and a partitionless container in another embodiment. This multiphase composition is stable upon storage and in a further embodiment is dispensed as a striped product where typically lather is reduced upon blending and a fatty acid is deposited onto the skin.

25 Claims, No Drawings

PACKAGED PRODUCT CONTAINING AN EXTRUDABLE MULTIPHASE COMPOSITION OF A FREE FATTY ACID PHASE AND A SOAP PHASE

BACKGROUND

1. Field of the Invention

The present invention relates to extrudable multiphase liquid cleansing compositions of the type typically used in skin and hair cleansing or shower gel compositions and which compositions contain both an acid and soap phase compositions that are separated.

2. Background of the Invention

Fatty acids are essential lipids that are necessary for skin health and function. Normally during washing, the action of surfactants is to remove essential fatty acids from the skin. Superfatted soap bars have been used to supply fatty acids to replace those stripped away during the washing process. It is known to produce free fatty acids in soap compositions by adding acid to the blend in order to produce such superfatted soap bars. For example, U.S. Pat. No. 3,694,367 describes a process where neutral soap in the fluid state can be blended with sulfonic acid to form a super fatted soap bar. PCT publication WO 95/02035 discloses the use of citric and other acids to form free fatty acids in a fat blend. PCT publication WO 97/11148 discloses the use of specific carboxylic acids to react with soap to form free fatty acids in the manufacture of a superfatted soap bar.

Surprisingly it was found that essential fatty acids may be deposited on the skin through the use of a liquid/semi-solid composition containing distinct acid and soap phases that are prevented from mixing until the composition is applied to the skin. Further it is observed that the lather volume of each of the separate phases is significantly reduced during product use after the phases are blended.

SUMMARY OF THE INVENTION

Applicants have discovered that a stable, extrudable multiphase product can be prepared having at least one high pH soap phase and at least one low pH acid phase. The term "multiphase product" is here defined as the combination of at least one acid phase composition and at least one soap phase composition that is contained in a container with or without a partition separating the phases but that the phases remain substantially separated and not blended with each other as is typified by e.g. colloidal dispersions or other intimate blends. "Stability" is here defined as the ability of the inventive multiphase product to maintain the separation of each phase from the other where they remain separated at room temperature for at least 70 days and at elevated temperature (50° C.) for at least one week. "Separated" as used herein is defined as the case where each distinct phase exists as a macro phase or volume element having an average dimension large enough to prevent substantial reaction of the acid and soap phases during storage of the product under the definition of Stability herein. Advantageously such an average dimension is about 2.0 mm, preferably about 5.0 mm and more preferably about 10.0 mm or greater. "Substantial reaction" is here defined as a reaction that is at least 30, 40, 50, 60, 70, 80 or 90% complete after storage of the product under the definition of Stability herein.

Therefore, in one aspect of the present invention is a packaged product of a stable, extrudable, multiphase aqueous liquid cleansing composition including, but not limited to a container having an outlet for dispensing the composition; an acid phase including at least one acid held within the container; a soap phase including at least one soap held within the container; and wherein the acid and soap phases are separated and exist as discrete macro phases. Advantageously the phases abut each other and may either be dispensed through the outlet in contact with each other or separately from each other. Preferably the phases are separated from each other in the container by a partition.

In another aspect of the invention is a method of depositing free fatty acids onto the skin while cleansing, including but not limited to the steps of:

a. providing an extrudable, multiphase, acid and soap cleansing composition product comprising a container; an acid phase including at least one acid; a soap phase including at least one soap; wherein the phases are separated;

b. dispensing the multiphase cleansing composition onto the skin so that the acid and soap phases mix with each other prior to or after contact with the skin to form a free fatty acid; and c. rubbing the composition on the skin for a time effective for depositing free fatty acid on the skin.

In a further aspect of the invention is a method for manufacturing a stable, extrudable, multiphase aqueous liquid cleansing composition, comprising the steps of:

a) adding in any sequence an acid phase including at least one acid to a container;

b) adding in any sequence a soap phase including at least one soap to the container; and c) wherein the acid and soap phases are separated.

Advantageously the container is either filled simultaneously or sequentially with the at least one acid phase and the at least one soap phase. Preferably the container is filled vertically or in a pulsating manner.

DETAILED DESCRIPTION OF THE INVENTION

In the present invention, the acid phase advantageously contains an acid selected from a carboxylic acid, an amino acid, a sulfonic acid, a phosphonic acid, an inorganic acid, or blends and salts thereof, preferably the acid is selected from citric acid, lactic acid, hexanoic acid, glycolic acid, hydrochloric acid, or aluminum sulfate. Preferably the acid phase has a pH of less than about 7, more preferably less than about 5. Advantageously the total concentration of the acid in the acid phase is in the range of about 0.1 to 20% by wt., preferably about 1.0 to 10% by wt. Preferably the lower limit of the acid in the acid phase is about 0.1, 0.2, 0.5, 0.7, 0.8, 1.0, 1.2 or 1.5% by wt. Preferably the upper limit of the acid in the acid phase is about 3, 4, 5, 6, 7, 8, 9, 10, 12, 15, 18 or 20% by wt. Advantageously the acid phase, the soap phase or both phases further comprise greater than about 0.1% by wt. (preferably greater than about 2% by wt.) of at least one nonsoap surfactant selected from an anionic, amphoteric, cationic or a mixture thereof. Preferably the upper limit for the total amount of nonsoap surfactant(s) is about 3, 4, 5, 7, 8, 10, 12, 15, 18, 20, 25 or 30% by wt. in the acid phase, the soap phase or both phases. Advantageously the sum of the anionic and amphoteric surfactant concentration in the acid phase, the soap phase or both phases is in the range of about 2 to 40% by wt. (preferably about 5 to 25% by wt.).

Advantageously soap phase contains a soap selected from a C8 to C50; to preferably a C12 to C22 alkanoic or alkenoic soap; more preferably selected from stearate, tallowate, cocoate, linoleate, arachidonate soap or a blend thereof. Preferably the soap phase has a pH of greater than about 7, preferably greater than about 8.5. Advantageously, the total concentration of the soap in the soap phase is in the range of about 0.1 to 50% by wt., preferably about 1 to 20% by wt. Preferably the lower limit of the soap in the soap phase is about 0.1, 0.2, 0.5, 0.7, 0.8, 1.0, 1.2 or 1.5% by wt. Preferably the upper limit of the acid in the acid phase is about 3, 4, 5, 6, 7, 8, 9, 10, 12, 15, 18 or 20% by wt.

Advantageously the stoichiometric ratio of the acid in the acid phase to soap in the soap phase is in the range of about 0.1 to 10 (preferably about 0.5 to 2) based on the total product composition.

Advantageously the sum of the anionic, amphoteric, and cationic surfactant concentration in the soap phase is in the range of about 0 to 25% (preferably about 5 to 20% by wt.) weight percent. Preferably the acid phase, the soap phase or both phases also include an occlusive emollient, a nonocclusive emollient, or a blend thereof in a concentration in the range of about 0.1 to 45% by wt. (preferably about 0.5 to 20% by wt.). Advantageously the lower limit of the occlusive emollient in the acid phase, the soap phase or both phases is about 0.1, 0.2, 0.5, 0.7, 0.8, 1.0, 1.2, 1.5, 2, 3, or 5% by wt. and the upper limit of the occlusive emollient in the acid phase, the soap phase or both phases is about 5, 10, 15, 20, 25, 30, 35, 40 or 45% by wt. Advantageously the lower limit of the nonocclusive emollient in the acid phase, the soap phase or both phases is about 0.1, 0.2, 0.5, 0.7, 0.8, 1.0, 1.2, 1.5, 2, 3, or 5% by wt. and the upper limit of the occlusive emollient in the acid phase, the soap phase or both phases is about 5, 10, 15, 20, 25, 30, 35, 40 or 45% by wt.

Preferably the occlusive emollients include triglyceride oils, fatty alcohols and esters, silicone oils, hydrocarbon oils or blends thereof. Preferably the non-occlusive emollients include polyhydric alcohols such as glycerine, glycols such as hexylene glycol, polyethylene glycols, saccharides and blends and derivatives thereof. Preferably the amphoteric surfactants are cocamidopropyl betaine, alkali is metal salts of C8 to C20 alkyl amphoacetates or a blend thereof. Preferably the anionic surfactant is selected from alkyl ether sulfate, alkyl sarcosinate, alkyl sulfosuccinate, alkyl sulfate or a blend thereof; the anionic surfactant having a counterion selected from an alkali metal, alkaline earth metal, ammonium, amine or blend thereof.

Advantageously the mixing of the contacting soap and acid phases is prevented across the interfacial boundary surfaces of the contacting phases when the composition is stored for 50° C. for 30 days.

Preferably the dispensed composition has at least about 1 weight percent of each of the acid and the soap phase contained therein. Advantageously each phase has a distinct physical appearance, preferably a distinct color. Advantageously there are only two phases in the container. Squeezing a flexible container holding the inventive product may dispense the product through a single or divided orifice but a single pump, or the like, is preferably used to dispense the product. When dispensed, each phase of the multiphase inventive product should be present in the concentration range of 1-99 weight %. In this manner, duality in the case of a two phase system, can be advantageously, economically, and visually communicated through a single container. A further advantage of using separate compositions is that elevated amounts of emollients can be added to the formula of one phase without affecting the stability of the other composition, even when the phases abut each other.

Advantageously the free fatty acid deposition on the skin as a result of the inventive method is in the range of about 0.1 to 1000 ug/cm2 (preferably in the range of about 1 to 1000 ug/cm2). Preferably the free fatty acid is generated at the level of greater than about 0.1 g fatty acid/100 g cleansing product (preferably greater than about 0.5 g fatty acid/100 g cleansing product).

Preferably the viscosity of each of the acid and the soap compositions have an upper limit of 300,000 cps at 25° C. in order to facilitate filling containers and dispensing with a conventional pump bottle. Preferably the acid and soap phases are rheologically compatible, i.e. they have the same flow properties under the conditions of filling, storage, and product usage.

The acid and soap phases preferably have different colors or other visual differences and preferably are filled vertically or in a pulsating manner in a single container with or without any partitions.

Surfactants

Soaps

The inventive product contains a soap in its soap phase. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. The soaps useful herein are the well known alkali metal salts of alkanoic or alkenoic acids having about 8 to 50 carbon atoms, preferably about 12 to about 22 carbon atoms. They may also be described as alkali metal carboxylates of alkyl or alkene hydrocarbons having about 12 to about 22 carbon atoms.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Anionic Surfactants

One or all of the phases may also contain anionic surfactants. The anionic surfactant (which may comprise about 3 to 40% by wt. of total composition) may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate, and the like.

The anionic may also be an alkyl sulfate (e.g., $C_{12}$-$C_{18}$ alkyl sulfate) or alkyl ether sulfate (including alkyl glyceryl ether sulfates), and the like. Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates, and the like.

Sulfosuccinates may be monoalkyl sulfosuccinates having the formula:

$$R^4O_2CCH_2CH(SO_3M)CO_2M,$$

amido-MEA sulfosuccinates of the formula $$R^4CONHCH_2CH_2O_2CCH_2CH(SO_3M)CO_2M$$

wherein $R^4$ ranges from $C_8$-$C_{22}$ alkyl and M is a solubilizing cation;

amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in U.S. Pat. No. 5,393,466, Titled "Fatty Acid Esters Of Polyalkoxylated Isethionic is Acid" issued Feb. 28, 1995 to Ilardi et al., hereby incorporated by reference into the subject application. This compound has the general formula:

$$RC\overset{O}{\overset{\|}{-}}O-\overset{X}{\overset{|}{C}}H-CH_2-(O\overset{Y}{\overset{|}{C}}H-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Zwitterionic and Amphoteric Surfactants

One or more of the phases may also contain zwitterionic/amphoteric surfactants. Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2-\overset{(R^3)_x}{\overset{\|}{Y^{(+)}}}-CH_2-R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-5-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1\!\!-\!\!\overset{O}{\overset{\|}{C}}\!\!-\!\!NH(CH_2)_n\!\!\overset{}{\underset{m}{\rfloor}}\!\!-\!\!\overset{R^2}{\underset{R^3}{\overset{|}{N^+}}}\!\!-\!\!X\!\!-\!\!Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

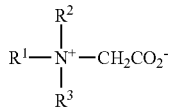

and amido betaines of formula:

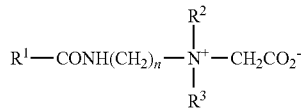

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl. A suitable betaine is cocoamidopropyl betaine.

A further possibility is that the amphoteric detergent is a sulphobetaine of formula

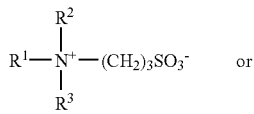

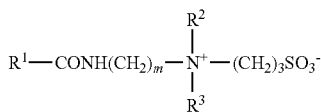

where m is 2 or 3, or variants of these in which —$(CH_2)_3$SO$^-_3$ is replaced by

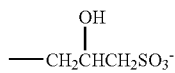

In these formulae $R^1$, $R^2$ and $R^3$ are as discussed previously.

Amphoacetates and diamphoacetates are also intended to be covered in possible zwitterionic and/or amphoteric compounds which may be used, especially C8-C20 amphoacetates or mixtures thereof, and the like. A suitable amphoacetate is sodium laurylamphoacetate.

The amphoteric/zwitterionic surfactant, when used, generally comprises about 2 to 30%, preferably about 3 to 20% by weight, more preferably about 3 to 10% of the composition.

A preferred surfactant system of the invention comprises the following: anionic surfactant (e.g. alkali metal alkyl ether-sulfate), about 2-50%; amphoteric surfactant (e.g. alkyl betaine or alkyl amphoacetate), about 3-20%.

The surfactant system may also optionally comprise a non-ionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called non-ionic detergent compounds include long chain tertiary amine oxides, long chain tertiary phosphine oxides and dialkyl sulphoxides, and the like.

The nonionic may also be a sugar amide, such as a polysaccharide amide. Specifically, the surfactant may be one of the lactobionamides described in U.S. Pat. No. 5,389,279 titled "Compositions comprising nonionic glycolipid surfactants" issued on Feb. 14, 1995 to Au et al. which is hereby incorporated by reference or it may be one of the sugar amides described in U.S. Pat. No. 5,009,814 titled "Use of n-polyhydroxyalkyl fatty acid amides as thickening agents for liquid aqueous surfactant systems" issued on Apr. 23, 1991 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 titled "Foaming surfactant compositions", issued on Jan. 21, 1986 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The nonionic comprises about 0 to 40% by wt. in each phase of the composition, preferably about 0 to 10% by wt.

Occlusive Emollients

One way of moisturizing is to reduce the rate of water loss from the stratum corneum (skin surface) by depositing an occlusive emollient on the skin surface which prevents water evaporation. Another technique is to add hygroscopic nonocclusive substances (humectants), which will retain water to the stratum corneum, making water available to the skin surface thereby producing the desired cosmetic effect. Non-occlusive emollients also function by improving the lubricity of the skin. Both occlusive and nonocclusive emollients as well as mixtures thereof are operative in the present invention and may be present in either or both phases. Examples of occlusive emollients include, lanolin and its derivatives, long chain esters, waxes, saturated and unsaturated fatty alcohols, conditioning oils and extracts, phospholipids, sterols, ceramides and silicones. The following occlusive emollients may optionally be suspended in the compositions of the invention.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and the like.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, and the like.

Animal Fats: acetylated lanolin alcohols, lanolin, lard, mink oil and tallow, and the like.

Other examples of occlusive emollients include mineral oil, petrolatum, silicone oil such as dimethyl polysiloxane, lauryl and myristyl lactate, fatty acid oils, triglycerides, and the like.

The occlusive emollient is generally used in an amount from about 0 to 70%, preferably about 5 to 40% by wt. of the phase in which it is found in. Generally, it should comprise no more than 70% of such phase. A portion of the emollient may be present in the form of solid or semi-solid beads. The beads are used in an amount from about 0 to 10%, preferably about 0 to 5%.

Nonocclusive Emollients

Some examples of nonocclusive emollients are liquid water-soluble polyols, glycerin, propylene glycol, sorbitol, polyethylene glycol, ethoxylated/propoxylated ethers of methyl glucose (eg., methyl gluceth-20) and ethoxylated/propoxylated ethers of lanolin alcohol e.g., Solulan-75). Some other preferred moisturizers are the nonoclusive liquid water soluble polyols and the essential amino acid to compounds found natural in the skin. Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl isopropyl esters of adipic, lactic, oleic, stearic, isostearic, myristic or linoleic acids, as well as many of their corresponding alcohol esters (sodium isostearoyl-2 lactylate, sodium capryl lactylate), hydrolyzed protein and other collagen-derived proteins, aloe vera gel and acetamide MEA. Other examples of both types occlusive and nonocclusive emollients are disclosed in "Emollients—a Critical Evaluation," by J. Mausner Cosmetics & Toiletries, May 1981, incorporated herein by reference.

In addition, the multiphase compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300), quaternary ammonium compounds; preservatives such as dimethyloldimethylhydantoin (Glydant XL1000), parabens, sorbic acid etc. Especially useful are skin care active ingredients that are activated by the change in pH observed when the phases are blended together during use. Any art recognized skin care active that may be activated to affect the condition of the skin by the pH change caused by the blending of the soap and acid phases and that is (are) stable in the phase containing the active may be suitably employed.

The compositions may also comprise coconut acyl mono- or diethanol amides and the like as suds boosters.

Antioxidants such as, for example, butylated hydroxytoluene (BHT) may be used advantageously in amounts of about 0.01% or higher if appropriate.

Cationic conditioners which may be used include Polyquaternium-10, Quatrisoft LM-200, Polyquaternium-24, Merquat Plus 3330, Polyquaternium 39, Ucare polymer JR-400, Jaguar® type conditioners and the like.

Another optional ingredient which may be added are the deflocculating polymers such as are taught in U.S. Pat. No. 5,147,576 titled "Liquid Detergent Composition In The Form Of Lamellar Droplets Containing A Deflocculating Polymer", issued on Sep. 15, 1992 to Montague, hereby incorporated by reference.

Other ingredients which may be included are exfoliants such as polyoxyethylene beads, silica particles, walnut shells and apricot seeds, and the like. pH and viscosity adjusters may be optionally used to e.g. adjust the pH of the separate phases prior to being combined into the inventive product. Such suitable pH adjusters may include citric acid, glycolic acid, lactic acid, other alpha or beta hydroxy acids, and the like.

The invention will now be described in greater detail by way of the following non-limiting examples. The examples are for illustrative purposes only and not intended to limit the invention in any way.

Except in the examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

Example 1

An inventive cleansing composition having a high pH soap phase and a low pH acid phase was prepared according to table 1. A combination of anionic and amphoteric surfactants were added to each phase. It was observed that the wt. % of free capric acid produced by the combination of the two phases was 1.2%. Furthermore, it was observed that when 50 g of the soap phase and 50 g of the acid phase were blended, 1.2 g of free capric acid was produced and made available for depositing onto the skin of the user.

TABLE 1

| Composition #1 Component | Concentration (wt. %) | |
| --- | --- | --- |
| | Soap phase- pH > 7.0 | Acid phase- pH < 7.0 |
| Sodium lauryl ether sulfate, 70% active | 5 | 3.5 |
| Sodium lauroamphoacetate, 30% active | 2.5 | 1.5 |
| Capric acid | 2.5 | 0 |
| Sodium hydroxide, 50% active | 2.5 | 0 |

TABLE 1-continued

| Composition #1 Component | Concentration (wt. %) | |
|---|---|---|
| | Soap phase- pH > 7.0 | Acid phase- pH < 7.0 |
| Citric acid | 0.2 | 1.5 |
| Fragrance | 0.5 | 0.5 |
| DMDM Hydantoin | 0.2 | 0.2 |
| EDTA , 39% active | 0.02 | 0.02 |
| EHDP, 61% active | 0.02 | 0.02 |
| Water | To 100% | To 100% |

Example 2

Another inventive cleansing composition having a high pH soap phase and a low pH acid phase was prepared according to table 2. A synthetic surfactant was added only to the acid phase.

TABLE 2

| Composition #2 Component | Concentration (wt. %) | |
|---|---|---|
| | Soap phase- pH > 7.0 | Acid phase- pH < 7.0 |
| Sodium lauroamphoacetate, 30% | 0 | 1 |
| Coconut fatty acid | 2.5 | 0 |
| Sodium hydroxide, 50% | 2.5 | 0 |
| Glycolic acid | 0 | 2.5 |
| DMDM Hydantoin | 0.2 | 0.2 |
| EDTA, 39% | 0.02 | 0.02 |
| EHDP, 61% | 0.02 | 0.02 |
| Water | To 100% | To 100% |

Example 3

An inventive cleansing composition having a high pH soap phase and a low pH acid phase can be prepared according to table 3. A synthetic surfactant has been added to both the soap and the acid phases.

TABLE 3

| Composition #3 Component | Concentration (wt. %) | |
|---|---|---|
| | Soap phase- pH > 7.0 | Acid phase- pH < 7.0 |
| Sodium lauroamphoacetate, 30% | 5 | 5 |
| Linoleic acid | 2.5 | 0 |
| Sodium hydroxide, 50% | 2.5 | 0 |
| Glycolic acid, 70% | 0 | 2.5 |
| DMDM Hydantoin | 0.2 | 0.2 |
| Fragrance | 0.5 | 0.5 |
| EDTA, 39% | 0.02 | 0.02 |
| EHDP, 61% | 0.02 | 0.02 |
| Water | To 100% | To 100% |

Example 4

An inventive cleansing composition having a high pH soap phase and a low pH acid phase was prepared according to table 4. A mild amphoteric surfactant was added only to the acid phase. The soap phase has a 1:2 molar ratio of fatty acid:NaOH to ensure complete conversion to soap. In this experiment, the ability to depress lather when the phases are blended is illustrated. The soap phase generates no lather. The acid phase provides 75 ml of lather volume measured according to the procedure below. When the 2 phases are combined, lather volume is dramatically reduced to 10 ml. Blending the two phases on the skin results in the deposition of a soft, waxy material which is the nascent fatty acid.

TABLE 4

| Composition #4 Component | Concentration (wt. %) | |
|---|---|---|
| | Soap phase- pH > 7.0 | Acid phase- pH < 7.0 |
| Sodium lauro amphoacetate, 30% | 0 | 2 |
| Isostearic acid | 47.33 | 0 |
| Sodium hydroxide, 50% | 13.33 | 0 |
| Glycolic acid, 70% | 0 | 50 |
| DMDM Hydantoin | 0.2 | 0.2 |
| Fragrance | 0.5 | 0.5 |
| EDTA, 39% | 0.02 | 0.02 |
| EHDP, 61% | 0.02 | 0.02 |
| Water | To 100% | To 100% |
| Lather (ml) | — | 75 |
| Lather (ml) combination | 10 | |
| Lathering depression coefficient | 0.13 | |

Lathering Depression Coefficient

Lathering depression may be quantified via the Lathering depression coefficient described below:

$$\text{Lathering depression coefficient} = L_{mix} / (L_a + L_s)$$
Where
  Acid phase lather volume = $L_a$
  Soap phase lather volume = $L_s$
  Combined phase lather volume = $L_{mix}$ When the soap and acid phases of the inventive composition are mixed, it is observed that the Lathering depression coefficient is less than or equal to 1, preferably in the range of about 0 to 0.2, more preferably in the range of about 0.5 to 1.0.

Lather volume measurement procedure is described below.

Procedure for Determining Lather Volume:

4 g of the either the acid or the soap phase is separately added to a 250 ml cylinder and 50 g water is gently added from the side to avoid foaming. The initial level of the liquid is noted. The mouth of the cylinder is then capped and inverted 10 times and then set on a level surface and the level of lather is immediately noted. The volume of lather above the initial level of liquid is the lather volume. Both phases may separately produce lather.

When the phases are blended, 2 g from each phase is transferred to the cylinder and stirred gently followed by lather determination as above.

Procedure for Determining Free Fatty Acid Concentration:

The soap and acid phases are mixed in equal amounts and dried. 50 mg of the dried material are added to a scintillation vial and a commercially available mixture of methanol and boron trichloride is added to the dried material, stirred and heated in a heating mantle for a 30 minutes at a sufficient temperature to form the methyl ester derivative using art recognized analytical methods. Heptane is then added and the heptane-containing ester is analyzed via gas chromatography to determine the level of capric or other fatty acids.

Viscosity Measurements

T-bar Viscosity Measurement

Scope:
This method covers the measurement of the viscosity of a phase composition that has lamellar structure.

Apparatus:
Brookfield RVT Viscometer with Helipath Accessory;
Chuck, weight and closer assembly for T-bar attachment;
T-bar Spindle A;
Plastic cups diameter greater than 2.5 inches.

Procedure:
1. Verify that the viscometer and the helipath stand are level by referring to the bubble levels on the back of the instrument.
2. connect the chuck/closer/weight assembly to the Viscometer (Note the left-hand coupling threads).
3. Clean Spindle A with deionized water and pat dry with a Kimwipe sheet. Slide the spindle in the closer and tighten.
4. Set the rotational speed at 0.5 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C.
6. Lower the spindle into the product (~¼ inches). Set the adjustable stops of the helipath stand so that the spindle does not touch the bottom of the plastic cup or come out of the sample.
7. Start the viscometer and allow the dial to make one or two revolutions before turning on the Helipath stand. Note the dial reading as the helipath stand passes the middle of its downward traverse.
8. Multiply the dial reading by a factor of 4,000 and report the viscosity reading in cps.

Cone and Plate Viscosity Measurement

Scope:
This method covers the measurement of the viscosity of a phase of the composition having isotropic structure.

Apparatus:
Brookfield Cone and Plate DV-II+Viscometer;
Spindle S41;
Plastic cups diameter greater than 2.5 inches.

Procedure:
1. Turn on Water Bath attached to the sample cup of the viscometer. Make sure that it is set for 25° C. Allow temperature readout to stabilize at 25° C. before proceeding.
2. With the power to the viscometer off, remove the spindle (S41) by turning counterclockwise.
3. Turn the power on and press any key as requested to autozero the viscometer.
4. When the autozero function is complete, replace the spindle (turning clockwise) and press any key.
5. Attach the sample cup. Using the up/down arrow keys, slowly change the speed to 10 rpm and press the SET SPEED key. Use the SELECT DISPLAY key so that the display is in % mode.
6. Turn the motor on. If the display jumps to 0.4% or higher or will not settle to 0±0.1%, turn the adjustment ring clockwise until it does.
7. Rotate the adjustment ring counterclockwise until the reading is fluctuating between 0.0 and 1.0%. The fluctuation must occur approximately every 6 seconds.
8. Turn the adjustment ring clockwise exactly the width of one division from the setting reached in step 7.
9. Turn the motor off. Using the up/down arrow keys, slowly change the speed to 0.5 rpm and press the SET SPEED key. Use the SELECT DISPLAY so that the display is in cP.
10. Place 2±0.1 g of product to be measured into the sample cup. Attach the cup to the viscometer.
11. Allow the product to remain in the cup with the motor OFF for 2 minutes.
12. Turn the motor ON and allow the spindle to turn for 2 minutes before noting the reading on the display.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:
1. A packaged product of a stable, extrudable, multiphase aqueous liquid cleansing composition, consisting essentially of:
   a) a container having an outlet for dispensing the composition;
   b) an acid phase including at least one acid held within the container;
   c) a soap phase including at least one soap held within the container;
   d) wherein the acid and soap phases are present in distinct macro phases whose average dimension is about 2.0 mm or greater, and are mixed with each other within the container; and
   e) wherein substantial reaction of the acid and soap phases with each other does not occur when the composition is stored for 50° C. for 30 days.
2. The product of claim 1 wherein the acid phase contains an acid selected from a carboxylic acid, an amino acid, a sulfonic acid, a phosphonic acid, an inorganic acid, or blends and salts thereof.
3. The product of claim 1 wherein the soap phase contains a soap selected from a C8 to C50 alkanoic or alkenoic soap.
4. The product of claim 1 wherein the acid phase has a pH of less than about 7.
5. The product of claim 1 wherein the soap phase has a pH of greater than about 7.
6. The product of claim 1 wherein the total concentration of the acid in the acid phase is in the range of about 0.1 to 20% by wt.
7. The product of claim 1 wherein the total concentration of the soap in the soap phase is in the range of about 0.1 to 50% by wt.
8. The product of claim 1 wherein the acid phase, the soap phase or both phases further comprise greater than about 0.1% by wt. of at least one nonsoap surfactant selected form an anionic, amphoteric, cationic or a mixture thereof.
9. The product of claim 1 wherein the stoichiometric ratio of the acid in the acid phase to soap in the soap phase is in the range of about 0.1 to 10 based on the total product composition.
10. The product of claim 8 wherein the sum of the anionic and amphoteric surfactant concentration in the acid phase, the soap phase or both phases is in the range of about 2 to 40% by wt.
11. The product of claim 8 wherein the sum of the anionic, amphoteric, and cationic surfactant concentration in the soap phase is in the range of about 0 to 25% by wt.

12. The product of claim 1 wherein the acid phase, the soap phase or both phases further comprise an occlusive emollient, a nonocclusive emollient, or a blend thereof in a concentration in the range of about 0.1 to 45% by wt.

13. The product of claim 8 wherein the amphoteric surfactant is selected from cocamidopropyl betaine, an alkali metal salt of C8 to C20 alkyl amphoacetate or a blend thereof.

14. The product of claim 8 wherein the anionic surfactant is selected from alkyl ether sulfate, alkyl sarcosinate, alkyl sulfosuccinate, alkyl sulfate or a blend thereof; the anionic surfactant having a counterion selected from an alkali metal, alkaline earth metal, ammonium, amine or a blend thereof.

15. The product of claim 1 wherein the dispensed composition has at least 1 weight percent of each of the acid and the soap phase contained therein.

16. The product of claim 1 wherein the container has a pump.

17. The product of claim 1 wherein each phase has a distinct physical appearance.

18. The product of claim 1 wherein each phase has a distinct color.

19. The product of claim 1 wherein there are only two phases.

20. A method of depositing free fatty acids onto the skin while cleansing, comprising the steps of:
  a) Providing an extrudable, multiphase, acid and soap cleansing composition product consisting essentially of a container, an acid phase including at least one acid, a soap phase including at least one soap, wherein the soap and acid phase are present in distinct macro phases whose average dimension is about 2.0 mm or greater, and are mixed with each other within the container; and wherein substantial reaction of the acid and soap phases with each other does not occur when the composition is stored for 50° C. for 30 days.
  b) Dispensing the multiphase cleansing composition onto the skin so that the acid and soap phases mix with each other prior to or after contact with the skin to form a free fatty acid; and
  c) Rubbing the composition on the skin for a time effective for depositing free fatty acid on the skin.

21. The method of claim 20 wherein the free fatty acid deposition on the skin is in the range of about 0.1 to 1000 ug/cm2.

22. The method of claim 20 wherein free fatty acid is generated at the level of greater than 0.1 g fatty acid/100 g cleansing product.

23. A method for manufacturing a stable, extrudable, multiphase aqueous liquid cleansing composition, comprising the steps of:
  a. Adding in any sequence an acid phase including at least one acid to a container;
  b. Adding in any sequence a soap phase including at least one soap to the container; and
  c. Wherein the cleansing composition consisting essentially of the acid and soap phases are present in distinct macro phases whose average dimension is about 2.0 mm or greater, and are mixed with each other; and wherein mixing of the contacting phases is prevented across the interfacial boundary surfaces of the contacting phases and wherein substantial reaction of the acid and soap phases does not occur when the composition is stored for 50° C. for 30 days.

24. The method of claim 23 wherein the container is either filled simultaneously or sequentially with the at least one acid phase and the at least one soap phase.

25. The method of claim 24 wherein the container is filled vertically or in a pulsating manner.

* * * * *